United States Patent [19]

Ohsaka et al.

[11] Patent Number: 4,946,972
[45] Date of Patent: Aug. 7, 1990

[54] PROCESS FOR DISTILLATION OF 2,2,3,3-TETRAFLUOROOXETANE

[75] Inventors: Yohnosuke Ohsaka, Ibaraki; Shoji Takaki, Takatsuki, both of Japan

[73] Assignee: Daikin Industries Ltd., Osaka, Japan

[21] Appl. No.: 299,353

[22] Filed: Jan. 23, 1989

[30] Foreign Application Priority Data

Jan. 23, 1988 [JP] Japan .................................. 63-12997

[51] Int. Cl.$^5$ .......................................... C07D 305/04
[52] U.S. Cl. ..................................... 549/511; 549/510
[58] Field of Search ................................ 549/511, 510

[56] References Cited

FOREIGN PATENT DOCUMENTS 0191490  8/1986  European Pat. Off. .
1097277  5/1986  Japan .................................... 549/510

OTHER PUBLICATIONS

Chemical Abstracts, vol. 105, No. 25, Dtd. 12/22/86, 105:226322e, "Separation of 2,2,3,3-Tetrafluorooxetane from Hydrogen Fluoride".

Chemical Abstracts, vol. 109, No. 12, Dtd. 9/19/88, 109:93808b, "Method of Making 2,2,3,3-Tetrafluorooxetane".

Primary Examiner—Richard L. Raymond
Assistant Examiner—Amelia A. Owens
Attorney, Agent, or Firm—Birch, Stewart, Kolasch & Birch

[57] ABSTRACT

A novel process for distillation of a mixture comprising 2,2,3,3-tetrafluorooxetane, which method comprises distilling the mixture comprising 2,2,3,3-tetrafluorooxetane in a metallic distillation column in the presence of at least one additive compound selected from the group consisting of an organic nitro compound and an aromatic compound.

4 Claims, No Drawings

PROCESS FOR DISTILLATION OF 2,2,3,3-TETRAFLUOROOXETANE

BACKGROUND OF THE INVENTION

1. Field of the Invention

The present invention relates to a process for distillation of a mixture comprising 2,2,3,3-tetrafluorooxetane (hereinafter referred to as merely "tetrafluorooxetane"). Particularly, the present invention relates to a process for distillation of the mixture comprising tetrafluorooxetane in which conversion of tetrafluorooxetane to trifluoropropionylfluoride is prevented.

2. Description of the Related Art

Tetrafluorooxetane is useful as a solvent or a raw material in the production of linear ethers, and can be commercially produced through a reaction of tetrafluoroethylene and paraformaldehyde in anhydrous hydrogen fluoride.

The product produced through the above reaction should be purified since it contains not only tetrafluorooxetane but also various other materials.

In order to purify such a product, a distillation process is usually employed. During the distillation operation, since a portion of tetrafluorooxetane may be converted to trifluoropropionylfluoride, it is desired to minimize the amount of tetrafluorooxetane to be converted.

SUMMARY OF THE INVENTION

It is, therefore, an object of the present invention to provide a process for distillation of a mixture comprising tetrafluorooxetane in which the conversion of tetrafluorooxetane to trifluoropropionylfluoride is efficiently prevented.

According to the present invention, there is provided a process for distillation of a mixture comprising tetrafluorooxetane, which method comprises distilling the mixture comprising tetrafluorooxetane in a metallic distillation column in the presence of at least one additive compound selected from the group consisting of organic nitro compounds and aromatic compounds.

As used herein, the term "mixture comprising tetrafluorooxetane" is intended to define a mixture of tetrafluorooxetane and the other materials in any ratio. Therefore, it defines not only a mixture which contains, as a main component, tetrafluorooxetane and, as trace components, the other materials, but also a mixture which contains a relatively smaller amount of tetrafluorooxetane and a relatively larger amount of the other materials.

DETAILED DESCRIPTION OF THE INVENTION

In the process of the present invention, it is advantageous to distill the mixture comprising tetrafluorooxetane in the presence of at least one organic nitro compound. Examples of the organic nitro compounds are nitromethane, nitroethane and nitrobenzene.

Alternatively, it is also advantageous to use at least one aromatic compound in place of the organic nitro compound. One preferred example of the aromatic compounds is a compound of formula:

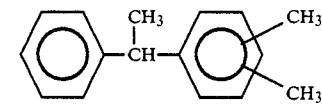

which is commercially available under the trademark "Nisseki-Hisol SAS-296" from Nippon Oil Co., Ltd, because of its high boiling point (296 ° C.) and its flame retardancy.

In addition, it is also possible to use any mixture consisting of the organic nitro compounds and the aromatic compounds as described above.

The process according to the present invention is particularly advantageous, when the mixture comprising tetrafluorooxetane is distilled in a metallic distillation column. It is preferable to use a distillation column made of stainless steel, for example SUS-316 (Japanese Industrial Standard).

Other distillation columns to be used in the process according to the present invention include a sieve tray column and a packed column.

With supplying continuously at least one suitable compound selected from the group consisting of the nitro compounds and aromatic compounds into the distillation column through an inlet at the top of the column, said compound can be present together with tetrafluorooxetane in the column, which prevents the tetrafluorooxetane from being converted to trifluoropropionylfluoride.

According to the present invention, it is preferred to supply at least one suitable compound in an amount of from 0.1 to 10% by weight, more preferably from 0.1 to 6% by weight, most preferably from 0.2 to 3% by weight based on the total amount of tetrafluorooxetane to be distilled.

According to the present invention, the amount of the tetrafluorooxetane converted to trifluoropropionylfluoride is drastically decreased, in contrast to the result obtained by employing the conventional distillation process in which any additional compound as described above is not used in the distillation column. For example, with the process of the present invention, the amount of converted tetrafluorooxetane to be converted is decreased to about from a fifth to a tenth.

The present invention will be hereinafter explained further in detail by following examples.

Example 1

Using a packed type distillation column made of SUS-316 (35 cm in diameter, the number of ideal plate being 15), a reaction product was distilled in batch operation. The reaction product was formed through the reaction in the presence of hydrogen fluoride and had a following composition:

| Tetrafluorooxetane | 260 kg |
| Hydrogen fluoride | 1330 kg |
| Others | 840 kg |

During the distillation, nitromethane was supplied to the column continuously at a rate of 1.5 kg/hr (totally 15 kg) through the inlet at the top of the column. Then, the weight ratio of nitromethane to tetrafluorooxetane to be distilled is equal to 0.058. From the top of the column, the mixture containing tetrafluorooxetane and hydrogen fluoride was recovered at a rate of 70 kg/hr as distillate. In total, the distillate recovered from the top of the column contained 250 kg of tetrafluorooxetane and 105 kg of hydrogen fluoride.

In comparison with the result obtained by employing the conventional distillation process in which no nitromethane is present in the column, with the process of the present invention, the amount of the tetrafluorooxetane converted to trifluoropropionylfluoride was decreased from 0.5% to 0.05% by weight based on the amount of tetrafluorooxetane to be distilled.

Example 2

The same reaction product as used in Example 1 was distilled with employing the same distillation apparatus under the same operation conditions as described in Example 1 except that in place of nitromethane, SAS-296 was supplied at a rate of 1.5 kg/hr (totally 15 kg) to the column (which corresponds to the weight ratio of 0.058 of SAS-296 to tetrafluorooxetane to be distilled).

In comparison with the result obtained by employing the conventional distillation process in which no SAS-296 is present in the column, with the process of the present invention, the amount of the converted tetrafluorooxetane was decreased from 0.5% to 0.1% by weight based on the amount of tetrafluorooxetane to be distilled.

What is claimed is:

1. A process for distillation of a mixture comprising 2,2,3,3-tetrafluorooxetane, which process comprises distilling the mixture comprising 2,2,3,3-tetrafluorooxetane in a metallic distillation column in the presence of at least one additive compound selected from the group consisting of nitromethane, nitroethane, nitrobenzene and

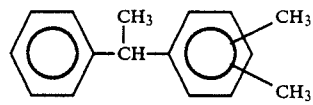

2. The process according to claim 1, in which said additive compound is supplied at an amount of from 0.1 to 10% by weight based on the weight of the 2,2,3,3-tetrafluorooxetane to be distilled.

3. The process according claim 1, in which said additive compound is supplied to the distillation column through an inlet at the top of the distillation column.

4. The process according to claim 1, in which the metallic distillation column is comprised of stainless steel.

* * * * *